United States Patent [19]

Trivedi et al.

[11] Patent Number: 4,501,735

[45] Date of Patent: Feb. 26, 1985

[54] N6-(1- AND 2-BENZOCYCLOALKYL) ADENOSINES

[75] Inventors: Bharat Trivedi, Canton; Harriet Hamilton, Chelsea; Walter Moos, Ann Arbor, all of Mich.

[73] Assignee: Warner-Lambert Company, Morris Plains, N.J.

[21] Appl. No.: 558,144

[22] Filed: Dec. 5, 1983

[51] Int. Cl.$^3$ ..................... A01N 31/00; A61K 31/70; C07H 19/06
[52] U.S. Cl. ......................................... 514/46; 536/26
[58] Field of Search ........................ 536/23, 24, 26, 27, 536/28, 29; 424/180, 181

[56] References Cited

U.S. PATENT DOCUMENTS

| | | | |
|---|---|---|---|
| 3,590,029 | 6/1971 | Koch et al. | 536/26 |
| 3,819,612 | 6/1974 | Imai et al. | 536/26 |
| 3,901,876 | 8/1975 | Vorbruggen et al. | 536/26 |
| 3,922,261 | 11/1975 | Pohlke et al. | 536/26 |
| 4,090,021 | 5/1978 | Vorbruggen | 536/28 |

FOREIGN PATENT DOCUMENTS

| | | | |
|---|---|---|---|
| 0040325 | 11/1981 | European Pat. Off. | 536/26 |
| 0062921 | 10/1982 | European Pat. Off. | 536/26 |
| 2402804 | 7/1975 | Fed. Rep. of Germany | 536/26 |
| 2406587 | 8/1975 | Fed. Rep. of Germany | 536/26 |
| 0046689 | 4/1975 | Japan | 536/24 |
| 7116563 | 6/1972 | Netherlands | 536/26 |
| 7210023 | 1/1973 | Netherlands | 536/26 |
| 2077726 | 12/1981 | United Kingdom | 536/26 |

OTHER PUBLICATIONS

Kampe et al., Pharmacological Adenosine Derivatives, Chem. Abstracts 71:124859x (1968).
Kikugawa et al., 6-Substituted Adenosines, Chem. Abstracts 81:78193g (1974).
Dumwiddie et al., Sedative and Anticonvulsant Effects of Adenosine Analogs in Mouse and Rat, Chem. Abstracts 96:116488b (1982).
Shikita et al., Hypotensive and Radioprotective Properties of N6-Substituted Adenosine Derivatives, Chem. Abstracts 82:325c (1974).
Vorbrueggen et al., N-(B-Inddyl and Imidazolylethyl)adenosines, Chem. Abstracts 79:32265n (1973).
Jahn, N6-(1-Naphthylmethyl)adenosine, An Adenosine Derivative with Prolonged Effects on Coronary Blood Flow, Chem. Astracts 71:89799d (1969).
Gough et al., Some Biologically Active N6-Methylated Adenosine Analogs, J. Med. Chem. 10, p. 475 (1967).
Letter et al., Ribosides of Some Cytotoxic Purine Derivatives, Chem. Abstracts 58:2499d (1962).
Pohlke et al., Heterocyclic-Substituted Adenosines, Chem. Abstracts 78:136628d (1973).

*Primary Examiner*—Delbert R. Phillips
*Assistant Examiner*—Charles H. Thieman
*Attorney, Agent, or Firm*—Ronald A. Daignault

[57] ABSTRACT

N$^6$-(1 and 2-Benzocycloalkyl)adenosines and pharmaceutically acceptable acid addition salts having highly desirable central nervous system and cardiovascular properties, process for their manufacture, pharmaceutical compositions and methods for using said compounds and compositions are described.

16 Claims, No Drawings

N6-(1- AND 2-BENZOCYCLOALKYL) ADENOSINES

BACKGROUND OF THE INVENTION

The compounds of the instant invention are adenosine analogs having some of the same activities as adenosine, but having a significantly longer duration of action. A distinguishing feature of these compounds from other adenosine analogs previously described, is the discovery that $N^6$-1 or 2-benzocycloalkyl adenosines have highly desirable central nervous system and cardiovascular activities, such as antipsychotic, sedative, antihypertensive, and antianginal.

U.S. Pat. No. 3,590,029 discloses $N^6$-(2-indanyl)-2-aminoadenosine having cardiac and circulatory activity. U.S. Pat. No. 3,922,261 discloses $N^6$-(1,2,3,4-tetrahydronaphthyl-2-)adenosine useful in reducing serum concentration of free fatty acids and triglycerides and improving coronary blood circulation. UK Pat. No. 2,077,726 discloses $N^6$-adenosine derivatives as antihypertensive agents. European patent publication EP No. 62,921 discloses $N^6$-adenosine derivatives that reduce blood pressure.

SUMMARY OF THE INVENTION

The present invention relates to a compound of the formula

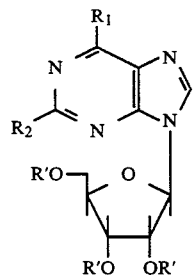

I where $R_1$ is of the formula

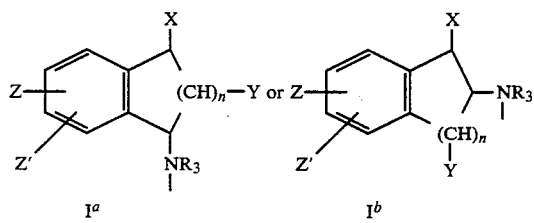

wherein n is 0 or 1; X is hydrogen, lower alkyl which may be terminally substituted by hydroxy, lower alkoxy, or carboxyl, OR where R is hydrogen, lower alkyl or acyl such as lower alkanoyl or benzoyl, phenyl, phenyl substituted by halogen, hydroxy, lower alkoxy, amino, or trifluoromethyl; Y is hydrogen, lower alkyl which may be terminally substituted by hydroxy, lower alkoxy, or carboxyl, OR where R is hydrogen or lower alkyl, or acyl such as lower alkanoyl or benzoyl; Z and Z' are independently hydrogen, halogen, nitro, trifluoromethyl, amino, lower alkyl, hydroxy, lower alkoxy; $R_2$ is hydrogen, halogen, $NR_1'R_2'$ where $R_1'$ and $R_2'$ are independently hydrogen, lower alkyl or aryl such as phenyl or substituted phenyl as defined above, SR where R is hydrogen or lower alkyl; $R_3$ is hydrogen or lower alkyl; R' is hydrogen, acetyl or benzoyl, or a pharmaceutically acceptable acid addition salt thereof; with the proviso that when $R_1$ is of the formula Ib, n is 1, X, Y, Z, Z', $R_3$ and R' are hydrogen, $R_2$ is hydrogen, halogen, SR where R is hydrogen or lower alkyl; its diastereomers or mixtures thereof, or a pharmaceutically acceptable acid addition salt thereof.

The present invention also relates to a pharmaceutical composition comprising a therapeutically effective amount of a compound of the above formula I with a pharmaceutically acceptable carrier and to a method of treating mammals by administering to such mammals a dosage form of a compound of the formula I as defined above.

DETAILED DESCRIPTION OF THE EMBODIMENTS

In the compounds of the formula I, the term "lower alkyl" is meant to include a straight or branched alkyl group having from 1 to 6 carbon atoms such as, for example, methyl, ethyl, propyl, isopropyl, butyl, sec-butyl, isobutyl, tertiarybutyl, amyl, isoamyl, neopentyl, hexyl, and the like.

Halogen includes particularly fluorine, chlorine or bromine.

Lower alkoxy is O-alkyl of from 1 to 6 carbon atoms as defined above for "lower alkyl".

Acyl is a group

and especially includes lower alkanoyloxy which is a straight or branched

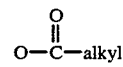

group of from 1 to 6 carbon atoms in the alkyl chain as defined above and benzoyl.

Aryl is an aromatic ring which may be unsubstituted or substituted. Specifically the term includes phenyl or phenyl substituted by halogen, hydroxy, lower alkoxy, amino, or trifluoromethyl.

The compounds of formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfonate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain one or more asymmetric carbon atoms at the $N^6$ side chain.

The invention includes individual diastereomers and mixtures thereof. The individual diastereomers may be prepared or isolated by methods known in the art.

A preferred embodiment of the present invention is a compound of the formula I, wherein $R_1$ is of the formula Ia and X, Y, Z, Z', n, $R_2$, $R_3$, and R' are as defined above or a pharmaceutically acceptable salt thereof.

Another preferred embodiment of the present invention is a compound of the formula I wherein $R_1$ is of the formula Ia; X, Y, Z, and Z' are hydrogen and n, $R_2$, $R_3$, and R' are as defined above.

Another preferred embodiment is a compound of formula I wherein $R_1$ is of the formula Ia; X, Y, Z, and Z' are hydrogen; $R_2$ is hydrogen, halogen, $NR_1'R_2'$ where $R_1'$ and $R_2'$ are independently hydrogen, lower alkyl or aryl, SR where R is hydrogen or lower alkyl; $R_3$ is hydrogen or methyl, and n and R' are as defined above.

Still another preferred embodiment is a compound of formula I wherein $R_1$ is of the formula Ia; X, Y, Z, and Z' are hydrogen, $R_2$ is hydrogen, chlorine, or amino; $R_3$ is hydrogen; n=1 and R' is as defined above.

A further preferred embodiment is a compound of formula I wherein $R_1$ is of the formula Ia; X, Y, Z, and Z' are hydrogen; $R_2$ is hydrogen, chlorine, or amino; $R_3$ is hydrogen; n=1 and R' is hydrogen.

A particular embodiment includes $N^6$-(1-indanyl)-adenosine or a pharmaceutically acceptable salt thereof.

A second generic embodiment of the present invention is a compound of the formula I, wherein $R_1$ is of the formula Ib; X, Y, Z, Z', $R_3$ and R' are as defined above, and when n is 0, $R_2$ is hydrogen, halogen, $NR_1'R_2'$ where $R_1'$ and $R_2'$ are independently hydrogen, lower alkyl or aryl, SR where R is hydrogen or lower alkyl; when n is 1, $R_2$ is hydrogen, halogen, SR where R is hydrogen or lower alkyl, or a pharmaceutically acceptable salt thereof.

Another preferred second generic embodiment of the present invention is a compound of the formula I, wherein $R_1$ is of the formula Ib; X, Y, Z, and Z' are hydrogen, and n, $R_2$, $R_3$ and R' are as defined above.

Another preferred second generic embodiment of the present invention is a compound of the formula I, wherein $R_1$ is of the formula Ib; X, Y, Z, and Z' are hydrogen; $R_3$ is hydrogen or methyl, and n, $R_2$ and R' are as defined above.

Still another preferred second generic embodiment is a compound of the formula I, wherein $R_1$ is of the formula Ib; X, Y, Z, Z' and $R_3$ are hydrogen; R' is as defined above, and when n is 1, $R_2$ is hydrogen or chlorine.

A further preferred second generic embodiment is a compound of the formula I, wherein $R_1$ is of the formula Ib; X, Y, Z, Z', $R_3$, and R' are hydrogen, and when n is 1, $R_2$ is hydrogen or chlorine.

A particular embodiment of the compounds of the formula I wherein $R_1$ is of the formula Ib is $N^6$-(2-indanyl)adenosine or a pharmaceutically acceptable salt thereof.

The compounds of formula I may be conveniently synthesized by reacting a 6-chloropurine riboside of formula II with a requisite amine of formula IIIA or IIIB in an inert solvent such as an alcohol or an aprotic solvent such as dimethyl formamide between 25° C. to 150° C. for 1 to 48 hours. It is useful to add a base such as triethylamine, tri-n-butylamine or potassium carbonate to neutralize the hydrogen halide formed as a by-product of the reaction. The reaction is illustrated as follows:

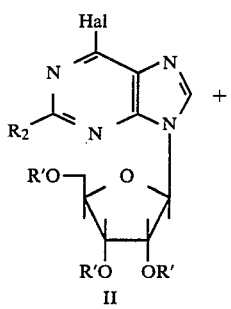

II

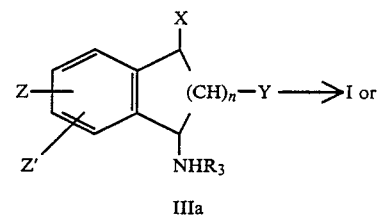

IIIa

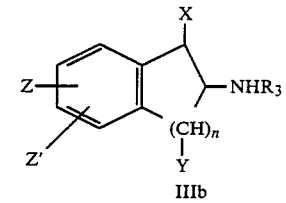

IIIb wherein Hal is halogen, preferably chlorine or bromine, R' is hydrogen, acetyl or benzoyl and X, Y, Z, Z', n and $R_2$ are as defined for formula I.

Compounds of the formula II, IIIa and IIIb are known or, if new, may be prepared by methods known in the art.

The compounds of formula I have been found to possess differing affinities at adenosine receptors (designated $A_1$ and $A_2$ receptors for convenience). These compounds are active in animal tests which are predictive of neuroleptic activity for the treatment of major psychoses such as schizophrenia. The compounds of the invention also have sedative/hypnotic properties and as such, are useful for the treatment of sleep disorders.

In addition, the compounds of the present invention are useful as antihypertensive agents for the treatment of high blood pressure. They also increase coronary blood flow and as such are useful in the treatment of angina and myocardial ischemia.

ANTIPSYCHOTIC EVALUATION

The antipsychotic activity of representative compounds of the invention was established by the Mouse Activity and Screen Test Procedure (MAST) described below.

Animals

Nine unfasted Swiss-Webster male mice weighing 20-30 g are equally divided into three groups for each drug dose to be tested. That is, data for each dose level was generated by three separate groups of three mice each.

Drugs

A minimum of three dose levels (10, 30, and 100 mg/kg) are tested for each drug. Treatments are administered intraperitoneally one hour prior to testing. All dosages are calculated as parent compound and given in volumes of 10 ml/kg. Compounds are dissolved or suspended in 0.2% Methocel. Control animals are injected with Methocel.

Testing: A two part testing procedure is started one hour postinjection. First, the screen test is performed (see *Pharmac. Biochem. Behav.* 6, 351–353, 1977). Briefly this test consists of placing mice on individual wire screens which are then rotated 180 degrees at the start of a 60 second observation period. The number of mice falling off the inverted screen is recorded.

Immediately following the screen test, the final phase of testing is initiated by placing each group of three mice in one actophotometer (*Life Sciences*, 22, 1067–1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten minute intervals for 60 minutes.

Data: The data obtained from the screen test are expressed as percent of mice falling off the screen. Data derived from locomotor activity of drug treated mice are compared to the activity of vehicle treated animals and are expressed as percent inhibition of spontaneous locomotion. All percentages reported for inhibition of locomotion are based upon data accumulated for one hour. The compounds are identified by example number.

| | ANTIHYPERTENSIVE EVALUATION | | |
|---|---|---|---|
| Example | Dose (mg/kg) | Inhibition of mouse locomotor activity | Screen test failure |
| 1 | 10 | 59% | 11% |
| | 30 | 88% | 0% |
| | 100 | 53% | 22% |
| 2 | 10 | 54% | 0% |
| | 30 | 84% | 33% |
| | 100 | 99% | 78% |

The usefulness of the compounds of the present invention as antihypertensive agents is demonstrated by their effectiveness in standard pharmacological test procedures, for example, in causing a significant decrease in mean arterial blood pressure in the conscious rat. This test procedure is described in the following paragraphs.

A METHOD FOR THE DIRECT MONITORING OF AORTIC BLOOD PRESSURE AND HEART RATE FROM CONSCIOUS RATS

The continuous monitoring of pulsatile blood pressure from unrestrained conscious rats surgically equipped with polyethylene cannulas was accomplished by means of a computer assisted data capture scheme (CADCS). The basic elements of the methodology are the cannulation procedure and the CADCS.

Method

Cannulation Procedure: Rats were anesthetized with Telazol (1:1 tiletamine HCl and zolazepam HCl); 20–40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scalulae (3-0 green braided suture). The midline incision was closed in two steps (muscle first, skin second) using continuous over and over sutures (4-0 chronic). Each rat was then given penicillin 30,000 units subcutaneously (Penicillin G Procaine Sterile Suspension).

The rats were fitted with a harness-spring-swivel assembly designed to protect the cannula and to provide the rat relative freedom of movement. The harnesses were fabricated from nylon hook and loop tape cemented to a metal plate to which spring wires (18-8 stainless steel), were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, MA) by means of PE100 tubing. While on test, each rat received a continuous slow infusion of heparinized saline solution (approximately 400 l or 40 units of heparin per 24 hour period) to prevent clot formation. Additional "flushes" of the cannula with heparinized saline were carried out when the aortic pulse pressure (systolic minus diastolic) was less than 25 mm Hg.

CADCS: The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer. The overall scheme involved modulating the primary signal from the pressure transducer, generating the primary data set of the one-minute values for systolic, diastolic, and mean blood pressures and heart rate by the in-lab microcomputer and the storage, analysis, and report generation by the main research computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow cannula. The distortion was 22–26 Hz and this provided a reliable estimate of both systolic and diastolic blood pressure.

The microcomputers (one for each of two groups of 16 rats) were connected to the input components through the module interface units, an analog-to-digital converter for the pressure wave form signal and the digital inputs for the dose and event marker switches. The microcomputer controlled the seqential acquisition of data from the modular interface units through an internal synchronous time-of-day clock/time base generator. Utilizing the time base generator as a reference, the blood pressure values and the marker switch status for each of the 32 stations were sampled every ten msec.

The microcomputer processed each blood pressure sample as it was received to produce "running average" values for heart rate, and mean, systolic and diastolic blood pressures.

When tested by the above procedure, compounds of Examples 1 and 2 produced the following changes in MAP and heart rate.

| mg/kg | | 1 | 3 | 5 | 7 | 9 |
|---|---|---|---|---|---|---|
| | | | | Hour | | |
| | | | Example 1 | | | |
| 3 | MAP | 25% | 15% | 18% | 9% | 13% |
| | HR | 30% ↓ | 11% ↓ | 6% ↓ | 7% ↑ | 9% ↑ |
| 10 | MAP | 29% | 23% | 24% | 19% | 2% |
| | HR | 39% ↓ | 42% ↓ | 44% ↓ | 25% ↓ | 13% ↓ |
| | | | Example 2 | | | |
| 10 | MAP | 26% | 17% | 18% | 15% | 18% |
| | HR | 12% ↓ | 1% ↑ | 4% ↓ | 8% ↑ | 1% ↑ |
| 30 | MAP | 33% | 21% | 18% | 14% | 19% |
| | HR | 18% ↓ | 10% ↓ | 5% ↑ | 4% ↓ | 8% ↓ |

CORONARY BLOOD FLOW

Method

Male rats (400-600 gms) are pretreated with Na heparin 2000 units and anesthetized with Na pentobarbital (50 mg/kg) administered intraperitoneally. Once anesthetized, the rat heart peritoneally. Once anesthetized, the rat heart is rapidly excised, the ascending aorta fitted to the aortic perfusion cannula, and secured with a ligature. The coronary arteries are perfused initially at a rate of about 15 ml/min for two to three minutes, after which they are perfused at constant pressure of 70 mm Hg and temperature of 37° C. The electrocardiogram (ECG) is recorded using two platinum electrodes positioned at the base and apex of the left ventricle. A second heart is excised, cannulated, and perfused by the same method outlined above. Both hearts are tested in parallel. The standard physiological salt solution (PSS) is a modified Krebs-Hanseleit bicarbonate buffer of the following composition in mM concentration: NaCl, 127; NaHCO$_3$, 25; dextrose, 5.5; Na Pyruvate, 2.0; KCl, 4.7; MgSO$_4$, 1.1; KH$_2$PO$_4$, 1.2; CaCl$_2$.2H$_2$O, 2.5; CaNa$_2$EDTA, 0.05.

A 30-minute stabilization period is observed before starting the test protocol.

MICROPROCESSOR CONTROLLED CORONARY PERFUSION AND DRUG DELIVERY SYSTEM

The microprocessor control system is a servo mechanism which permits coronary perfusion pressure (CPP) and drug concentration to be maintained constant independent of changes in coronary flow. The level at which CPP and drug concentration are maintained can be changed by commands communicated through the microprocessor keyboard. Dose-response curves are carried out by perfusing concentrated drug solution (DC) at rates proportional to total coronary flow (CF$_T$). Drug concentrations are increased by proportionate increases in the rate of DC infusion over CF$_T$ via the microprocessor keyboard. The proportional flow rates for DC:CF$_T$ is about 0.0002:1 at the low end and 0.02:1 at the high end of the dose-response curve. Dose-response curves encompassing at least two log doses are carried out by preparing two DCs with a concentration difference of 1:100. Following the first dose range of two log doses, the DC are switched, proportional pumping rate adjusted, and the dose-response curve continued for another two log doses. The standard dose-response curve is carried out in one-half log dose increments starting at a subthreshold dose and ending at a dose which produces near maximal response in activity. Standard reference compounds are tested over the range of $10^{-9}$ to $10^{-6}$M.

MEASUREMENTS

Measurements are for heart rate (HR) and coronary flow (CF). Units are: HR, beats/minute (bpm) and CF, milliliters/minute (ml/min). HR is calculated from the ECG strip chart recording and CF is calculated by recording analog outputs from pumps 1 and 2. Outputs from pump #1=CF$_T$ and the output from pump #2=CF for heart B (CF$_B$). CF for heart A (CF$_A$) is calculated (CF$_T$−CF$_B$=CF$_A$).

Using the above technique, the effects of the compound of Examples 1 and 2 are as follows:

| Dose (Molar) | Example 1 | | Example 2 | |
|---|---|---|---|---|
| | CF | HR | CF | HR |
| 1 × 10$^{-8}$ | 3% | −3% | 2% | −1% |
| 3 × 10$^{-8}$ | 9% | −9% | 7% | −5% |
| 1 × 10$^{-7}$ | 18% | −19% | 16% | −11% |
| 3 × 10$^{-7}$ | 29% | −25% | 24% | −21% |
| 1 × 10$^{-6}$ | 35% | −52% | 29% | −36% |
| 3 × 10$^{-6}$ | 35% | −67% | 30% | −56% |

Accordingly, the present invention also includes a pharmaceutical composition for treating psychoses, sleep disorders, hypertension or angina comprising a corresponding antipsychotic, sedative, antihypertensive or antianginal effective amount of a compound of the formula I as defined above together with a pharmaceutically acceptable carrier.

The present invention further includes a method for treating psychoses, sleep disorders, hypertension, or angina in mammals suffering therefrom comprising administering to such mammals either orally or parenterally a corresponding pharmaceutical composition containing a compound of the formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid dose may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizng agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

N(6)-(2-Indanyl)adenosine

Two grams 6-chloropurine riboside, 1.48 grams 2-aminoindane hydrochloride and 1.74 g triethylamine are refluxed in ethanol under nitrogen for 20 hours. Upon cooling, solid material crystallizes. The reaction mixture is diluted with 70 ml ethanol, filtered and washed with ethanol. Solid thus obtained is suspended in approximately 25 to 30 ml methanol, filtered, and washed with methanol and dried affording 1.95 g (73%) N(6)-(2-indanyl)adenosine having a melting point of 166°–168° C.

Anal. Calcd for $C_{19}H_{21}N_5O_4$: C, 59.52; H, 5.52; N, 18.26; Found: C, 59.26; H, 5.61; N, 18.19.

EXAMPLE 2

N(6)-(1-Indanyl)adenosine

Four grams 6-Chloropurine riboside, 2.32 g 1-aminoindane and 2.11 g of triethylamine are refluxed in 100 ml of absolute ethanol under nitrogen for 20 hours. Volatiles are evaporated to dryness. Residue is dissolved in 20 ml 2-propanol and diluted with 200 ml $H_2O$. Clear aqueous solution is decanted and residual oily material is washed with cold water. Coevaporation with ethanol several times gives solid material. Crystallization from $CHCl_3$/2-propanol (10:1) and hexane affords 3.0 g (56.2%) N(6)-(1-indanyl)adenosine having a melting point of 120°–122° C. (foam).

Anal. Calcd for $C_{19}H_{21}N_5O_4$: C, 59.52; H, 5.52; N, 18.26; Found: C, 59.37; H, 5.48; N, 18.00.

EXAMPLE 3

N(6)-(1-Indanyl)-2-aminoadenosine

A mixture of 2.0 g of 6-Chloro-2-aminopurine riboside, 1.1 g of 1-aminoindane and 1.0 g of triethylamine are refluxed in 50 ml ethanol under nitrogen for 20 hours. The solvent is evaporated and the residue is treated with 100 ml of cold water. The solid material thus obtained is filtered, dried, and purified by flash chromatography on silica gel. The product is eluted with 5% methanol-chloroform. Evaporation of the solvent from the pure fractions followed by crystallization from chloroform-hexane affords 1.9 g (72%) of N(6)-(1-indanyl)-2-aminoadenosine; having a melting point of 143°–146° C.

Anal. Calcd for $C_{19}H_{22}N_6O_4 \cdot 0.3H_2O$: C, 56.51; H, 5.64; N, 20.80 Found: C, 56.90; H, 6.06, N, 20.38.

EXAMPLE 4

(S)(+)-1-Aminoindane and (R)(−)-1-Amino-indane (S)(+)-1-aminoindane and (R)(−)-1-aminoindane are obtained lby the resolution of (±)-1-aminoindane using N-acetyl-leucine.[1]

[1] V. Ghislandi and d. Vercesi, *Bull. Chim. Farm.* 115, 489–500, 1976.

N(6)-[1-(S)-indanyl]adenosine

For 20 hours, 0.92 g 6-chloropurine riboside, 0.45 g (S) (+)-1-aminoindane, and 0.38 g triethylamine in 25 ml absolute ethanol are refluxed under nitrogen. The solvent is evaporated to dryness and the residue is treated with 50 ml cold water. Clear aqueous solution is decanted from the organic material. It is dissolved in ethanol and evaporated to dryness and the residue is purified using flash chromatography on silica gel. The compound is eluted with 5% MeOH-CHCl$_3$. Evaporation of the solvent from pure fractions affords solid material which is crystallized from a mixture of CHCl$_3$-MeOH and hexane yielding 0.73 g (59.5% of theory) N(6) [1(S)-indanyl]adenosine having a melting point of 125°–127° C.

Anal. Calcd for C$_{19}$H$_{21}$N$_5$O$_4$.0.25 CHCl$_3$: C=55.94; H=5.18; N=16.74; Found: C=55.57; H=5.30; N=16.61.

N(6)-[1-(R)-indanyl]adenosine

For 20 hours, 1.83 g 6-chloropurine riboside, 0.95 g (R)(−)-1-aminoindane and 0.862 g triethylamine are refluxed in 50 ml absolute ethanol under nitrogen atmosphere. The solvent is evaporated to dryness and residue is treated with 50 ml cold water. The solid material is filtered, dissolved in excess ethanol, and volatiles are evaporated under reduced pressure to remove water. Residue upon treatment with ethanol affords solid material. It is filtered and dried. One more crop of the same material is obtained from the mother liquor yielding 1.46 g (60% of theory) of N(6) [1-(R)-indanyl]adenosine having a melting point of 185°–187° C.

Anal. Calcd for C$_{19}$H$_{21}$N$_5$O$_4$: C=59.52; H=5.52; N=18.26; Found: C=59.00; H=5.50; N=18.05.

We claim:

1. A compound of the formula

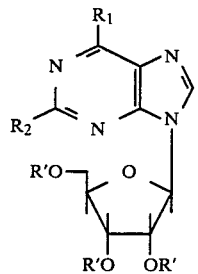

wherein R$_1$ is of the formula

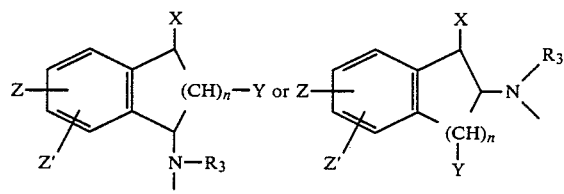

in which n is 1; X is hydrogen, lower alkyl or lower alkyl terminally substituted by hydroxy, lower alkoxy or carboxyl, OR where R is hydrogen, lower alkyl, lower alkanoyl or benzoyl, phenyl or phenyl substituted by halogen, hydroxy, lower alkoxy, amino or trifluoromethyl; Y is hydrogen, lower alkyl or lower alkyl terminally substituted by hydroxy, lower alkoxy, or carboxyl, OR where R is hydrogen, lower alkyl, lower alkanoyl or benzoyl; Z and Z' are independently hydrogen, halogen, nitro, trifluoromethyl, amino, lower alkyl, hydroxy or lower alkoxy; R$_3$ is hydrogen or lower alkyl; R' is hydrogen, acetyl or benzoyl; R$_2$ is hydrogen or halogen; its diastereomers or mixtures thereof, or a pharmaceutically acceptable acid addition salt thereof.

2. A compound of the formula

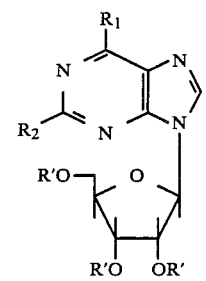

wherein R$_1$ is of the formula

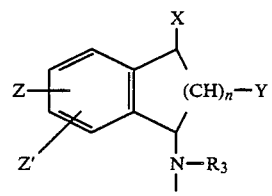

in which n is 1; X is hydrogen, lower alkyl or lower alkyl terminally substituted by hydroxy, lower alkoxy or carboxyl, OR where R is hydrogen, lower alkyl, lower alkanoyl or benzoyl, phenyl or phenyl substituted by halogen, hydroxy, lower alkoxy, amino or trifluoromethyl; Y is hydrogen, lower alkyl or lower alkyl terminally substituted by hydroxy, lower alkoxy, or carboxyl, OR where R is hydrogen, lower alkyl, lower alkanoyl or benzoyl; Z and Z' are independently hydrogen, halogen, nitro, trifluoromethyl, amino, lower alkyl, hydroxy or lower alkoxy; R$_3$ is hydrogen or lower alkyl; R' is hydrogen, acetyl or benzoyl, and R$_2$ is hydrogen or halogen; its diastereomers or mixtures thereof, or a pharmaceutically acceptable acid addition salt thereof.

3. A compound as claimed in claim 2, wherein X, Y, Z, and Z' are hydrogen.

4. A compound as claimed in claim 3, wherein R$_2$ is hydrogen or chlorine; R$_3$ is hydrogen, and n 1.

5. A compound as claimed in claim 4, wherein R' is hydrogen.

6. A compound as claimed in claim 5, and being N$^6$-(1-indanyl)adenosine.

7. A compound as claimed in claim 6, and being N$^6$-[1-(S)-indanyl]adenosine.

8. A compound as claimed in claim 6, and being N$^6$-[1-(R)-indanyl]adenosine.

9. A compound of the formula

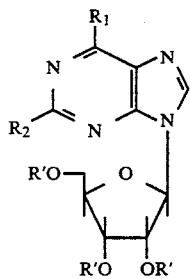

wherein $R_1$ is of the formula

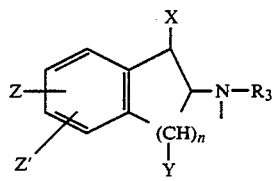

in which n is 1 X is hydrogen, lower alkyl or lower alkyl terminally substituted by hydroxy, lower alkoxy or carboxyl, OR where R is hydrogen, lower alkyl, lower alkanoyl or benzoyl, phenyl or phenyl substituted by halogen, hydroxy, lower alkoxy, amino or trifluoromethyl; Y is hydrogen, lower alkyl or lower alkyl terminally substituted by hydroxy, lower alkoxy, or carboxyl, OR where R is hydrogen, lower alkyl, lower alkanoyl or benzoyl; Z and Z' are independently hydrogen, halogen, nitro, trifluoromethyl, amino, lower alkyl, hydroxy or lower alkoxy; $R_3$ is hydrogen or lower alkyl; R' is hydrogen, acetyl or benzoyl; $R_2$ is hydrogen or halogen; its diastereomers or mixtures thereof, or a pharmaceutically acceptable acid addition salt thereof.

10. A compound as claimed in claim 9, wherein X, Y, Z, and Z' are hydrogen.

11. A compound as claimed in claim 10, wherein $R_3$ is hydrogen or methyl.

12. A compound as claimed in claim 10, wherein $R_3$ is hydrogen, and $R_2$ is hydrogen or chlorine.

13. A compound as claimed in claim 11, wherein R' is hydrogen.

14. A compound as claimed in claim 12, and being $N^6$-(2-indanyl)adenosine.

15. A pharmaceutical composition comprising an antihypertensive effective amount of a compound according to claim 1 together with a pharmaceutically acceptable carrier.

16. A method for treating hypertension in mammals suffering therefrom comprising administering to such mammals a pharmaceutical composition according to claim 13.

* * * * *